United States Patent [19]
Masson

[11] Patent Number: 5,937,530
[45] Date of Patent: Aug. 17, 1999

[54] KINEMATIC RESTRAINT DEVICE AND METHOD FOR DETERMINING THE RANGE OF MOTION OF A TOTAL KNEE REPLACEMENT SYSTEM

[76] Inventor: Martin Masson, 90 Tiffany Blvd., Apt. 174, Newark, N.J. 07104

[21] Appl. No.: 08/979,692

[22] Filed: Nov. 26, 1997

[51] Int. Cl.⁶ .............................. A61B 5/103; G01B 5/24
[52] U.S. Cl. ................. 33/534; 33/512; 33/1 N; 73/865.9; 623/20; 606/53; 606/102
[58] Field of Search ............................. 33/512, 511, 1 N, 33/534; 73/1, 79, 865.4, 865.9; 606/102, 53; 623/20, 18, 16

[56] References Cited

U.S. PATENT DOCUMENTS

| | | | |
|---|---|---|---|
| 4,834,057 | 5/1989 | McLeod, Jr. | 33/512 |
| 4,940,063 | 7/1990 | Challis | 33/512 |
| 5,423,828 | 6/1995 | Benson | 606/102 |
| 5,514,183 | 5/1996 | Epstein et al. | 623/20 |
| 5,603,717 | 2/1997 | Benson | 33/512 |
| 5,813,124 | 9/1998 | Freitag | 33/534 |

*Primary Examiner*—Christopher W. Fulton
*Attorney, Agent, or Firm*—Pennie & Edmonds LLP

[57] ABSTRACT

A kinematic restraint device and method for determining the range of motion of a total knee replacement system are disclosed. The kinematic restraint device is used as a surrogate knee that duplicates the elastic behavior of individual ligaments, tendons, muscles related to a human knee. The kinematic restraint device according to the invention includes a total knee replacement system and at least one cable or cable-spring combination representing a ligament, tendon, or muscle component of the human knee. The kinematic restraint device overcomes hurdles posed by the use of natural knees in pre-operatively determining the range of motion of a total knee replacement system. Furthermore, an outer membrane is used to simulate the viscoelastic effects exhibited by fibrous structures, fatty tissues, and muscle mass enveloping the joint on the total knee replacement kinematics.

22 Claims, 5 Drawing Sheets

KINEMATIC RESTRAINT DEVICE AND METHOD FOR DETERMINING THE RANGE OF MOTION OF A TOTAL KNEE REPLACEMENT SYSTEM

FIELD OF THE INVENTION

This invention relates to testing total knee replacement systems. More particularly, it relates to an apparatus and method for determining the range of motion of a total knee replacement system and estimating joint kinematics before total knee arthroplasty.

BACKGROUND OF THE INVENTION

Human joints are susceptible to degenerative diseases. Arthritis affecting the knee often causes such pain and discomfort that older patients cannot maintain an independent lifestyle. For these patients, total knee arthroplasty provides an opportunity to restore the knee's functions and lost mobility. Today's orthopaedic surgeon has a wealth of options for customizing surgery to a wide range of patient's anatomies and conditions. The knee system elected must meet the requirements for articular stability and anatomic pathways tracking. However, these two requirement are inherently conflicting. Stability is accomplished through articular conformity and maximum contact area while anatomic tracking is realized through unconstrained mobility.

Total knee replacement systems can usually be grouped under two denominations: condylar and stabilized. Each is tailored to individual needs and preferences. Condylar prostheses provide maximum range of motion. Their usage is indicated with patients who do not need compensation for ligamentous instability. Stabilized tibial prostheses have a central stabilizer post. Minimal clearance between the post and the femoral housing provides increased stability in the anterior-posterior and medial-lateral directions and constrains internal-external rotations. Such prostheses are useful when little reliance is placed on the surrounding soft tissues to stabilize the joint. Although both prostheses have analogously shaped bearing surfaces, the condylar prostheses rely mostly upon the surrounding tendons and ligaments to maintain the knee joint's integrity and to impart stability to the knee during movement.

The three-dimensional kinematics of the prosthetic knee are the result of a delicate harmony between component selection, placement, orientation, and ligament balancing. As the knee flexes, ligaments across the knee joint are sequentially applied. The length and orientation of ligaments allow functional motions and yet provide restraints at the limits of such motions. Conversely, slight variations in component placement or orientation may affect the ligaments' operation. Differences in the radii of curvatures and congruency of the articulating profiles can also induce substantial changes in rotation and translation. Complications arise when the mechanics of the ligaments are not in tune with the mechanics of the total knee geometries. For instance, misplacement or misalignment may cause the ligaments to become highly loaded or overly lax within the functional range of motion.

Success in restoring a knee's normal function can be measured by assessing the post-arthroplasty kinematic signature of a specific implant and comparing it to normal gait kinematics. This kinematic profile is revealed as each component's geometry comes into contact. While it is generally simple to measure the spatial motion of the lower extremity post-operatively, it is more difficult to estimate or predict the functional outcome of a surgical implantation before it is actually performed on the patient.

In the prior art, an in vitro technique for estimating the relative three-dimensional in vivo displacements of a particular total knee system is proposed. The current test method requires the use of natural knee specimens, either fresh or embalmed, to quantify the range of motion of a total knee replacement system. This method has numerous drawbacks. The procedure is lengthy and requires considerable surgical skills. The handling of human specimens presents a potential risk from blood borne pathogens. Moreover, a natural knee may not be implanted more than once. Reproducibility is a major issue as considerable variations are to be expected from specimen to specimen or from day to day. Indeed, because the natural knee presents variations in freshness, quality, size, age, and gender, this procedure is not reliable.

The present invention relieves the concerns associated with using cadaveric specimens for assessment of total knee kinematics. A departure from prior testing grounds is signalled by using a synthetic knee in place of a natural knee. The present application is based on the finding that it is possible to replicate the primary constraints of the knee using synthetic materials and appropriate design principles. Since ligaments are major structures which limit knee kinematics, one needs to duplicate their elastic behavior, placement, and orientation, in order to impart a standardized confining pattern. Hence, the synthetic knee acts as a surrogate joint to receive the total knee replacement prior to measuring its kinematic profile. The present invention overcomes hurdles posed by natural knee sample disparities, biohazards, and surgical skills.

SUMMARY OF THE INVENTION

It is an object of the present invention to utilize a kinematic restraint device to overcome hurdles posed by the use of natural knees while determining the range of motion of a total knee replacement system.

It is also an object of the present invention to relieve biosafety concerns associated with the use of natural cadaveric knees by developing a surrogate synthetic model for the knee joint.

It is yet another object of the present invention to provide an apparatus that reduces experimental errors caused by disparities in natural knees in the course of determining the range of motion of a total knee replacement system.

It is yet another object of the present invention to provide an apparatus that does not require the user to possess surgical skills in the course of determining the range of motion of a total knee replacement system.

It is yet another object of the present invention to provide an apparatus that provides greater flexibility to the user to simulate different surgical placement and orientations of a total knee replacement system under different soft tissue conditions.

It is yet another object of the present invention to develop a technique for measuring the range of constraint or the range of motion of total knee replacement system components under different conditions of forces and torques at specific flexion angles.

It is yet another object of the present invention to develop a technique for measuring the three-dimensional motion path of a total knee replacement system which is being submitted to force and torque profiles typical of physiologic activities.

It is yet another object of the present invention to develop a technique for simulating passive soft tissue restraints associated with normal or pathological conditions, or certain types of trauma.

It is yet another object of the present invention to impart a standardized confining pattern for in vitro wear studies of total knee replacement systems.

The kinematic restraint device for determining the range of motion of a total knee replacement system according to the present invention comprises a set of total knee replacement system assembly fixtures, a total knee replacement system, at least one combination of a cable and a spring connected thereto representing at least one ligament, tendon, or muscle component related to the human knee, and means for affixing the cable-spring combination on the total knee replacement system assembly fixtures. The set of total knee replacement system assembly fixtures comprises a femoral holder and a tibial holder. The cable-spring combination has predetermined mechanical properties of the ligament, tendon, or muscle component which it represents. Such mechanical properties include tensile stiffness, viscoelasticity, strain, strength and yield modulus.

In a first preferred embodiment of the invention, the total knee replacement system comprises a femoral component and a tibial component, each of which has a contact surface thereof. The femoral component is affixed to one end of the femoral holder, and the tibial component is affixed to one end of the tibial holder. The contact surface of the femoral component is in contact with the contact surface of the tibial component to form a condyloid joint to simulate a human knee.

At least one cable-spring combination is used to represent at least one ligament selected from the group consisting of the anterior cruciate ligament, the posterior cruciate ligament, the medial collateral ligament, and the lateral collateral ligament. It is preferred that a plurality of cable-spring combinations are used simultaneously to represent a multistrand aspect of a single ligament. It is also preferred that two, three, or four cable-spring combinations are used simultaneously to represent more than one ligament.

In the kinematic restraint device embodiment of the present invention, cylindrical collars and cable assemblies are used to affix the cable-spring combination to join the total knee replacement system. A cylindrical collar is affixed to the femoral holder by a plurality of set screws. The spring used is a hollow compressive cylindrical core which has predetermined compressive properties to simulate the tensile properties of a specific ligament of the human knee. The spring is positioned in a through-hole on the collar. A similar cylindrical collar and spring are used on the tibial holder. An end fitting is attached to the cable and movably attached to the spring. The cable first passes through the compression spring of the femoral holder, then the compression spring of the tibial holder, and finally it terminates at another end fitting.

In a second preferred embodiment of the invention, the total knee replacement system comprises a femoral component having a contact surface, a tibial component having a contact surface, and a patella having a contact surface. The femoral component is affixed to one end of the femoral holder, and the tibial component is affixed to one end of the tibial holder. The contact surface of the femoral component is in contact with the contact surface of the tibial component to form a condyloid joint to simulate a human knee. The patella is positioned anteriorly and superiorly on the condyloid joint. The contact surface of the patellar component is in contact with the contact surface of the femoral component to form a patellofemoral joint to simulate a partial arthrodial articulation.

At least one cable-spring combination is used to represent at least one ligament selected from the group consisting of the anterior cruciate ligament, the posterior cruciate ligament, the medial collateral ligament, and the lateral collateral ligament. It is preferred that a plurality of cable-spring combinations are used simultaneously to represent a multistrand aspect of a single ligament. It is also preferred that two, three, or four cable-spring combinations are used simultaneously to represent more than one ligament.

It is preferred to simultaneously use both the cable-spring combination and a cable for the patella in this embodiment. In this regard, at least one cable connects the patella to the femoral and tibial holders via a fastener. The cable has predetermined properties that allows normal patellar tracking similar to that of the natural knee.

In a third preferred embodiment of the invention, the total knee replacement system comprises a femoral component having a contact surface, a tibial component having a contact surface, and a patella having a contact surface. The femoral component is affixed to one end of the femoral holder, and the tibial component is affixed to one end of the tibial holder. The contact surface of the femoral component is in contact with the contact surface of the tibial component to form a condyloid joint to simulate a human knee. The patella is positioned anteriorly and superiorly on the condyloid joint. The contact surface of the patellar component is in contact with the contact surface of the femoral component to form a patellofemoral joint to simulate a partial arthrodial articulation.

A cable connects the patella to the tibial holder via a fastener and to an actuator via a fastener. The cable has a predetermined stiffness characteristic of the patellar tendon. The actuator applies tensile forces similar to those applied by the quadriceps muscle group in the natural knee.

In a fourth preferred embodiment, the kinematic restraint device for determining the range of motion of a total knee replacement system according to the invention further comprises an outer membrane that ensheathes the total knee replacement system and the cable to simulate the combined damping effects of fibrous structures, fatty tissues, and muscle mass enveloping the knee joint on the total knee replacement kinematics. The outer membrane comprises a composite structure and a plurality of flexible tensioners embedded therein. The composite structure helps guide the cables by means of the flexible tensioners. A material with anisotropic properties such as neoprene can be used for the composite structure. The composite structure can be filled with gel or other material to further approximate non-linear properties exhibited by soft tissues.

BRIEF DESCRIPTION OF THE DRAWINGS

These and other objects, features and elements of the present invention will be better understood from the following detailed description of preferred embodiments of the invention in which.

DETAILED DESCRIPTION OF PREFERRED EMBODIMENTS

The kinematic restraint device for determining the range of motion of a total knee replacement system according to the present invention comprises a set of total knee replacement system assembly fixtures, a total knee replacement system, at least one combination of a cable and a spring connected thereto representing at least one ligament, tendon, or muscle component related to the human knee, and means for affixing the cable-spring combination on the total knee replacement system assembly fixtures. The set of total knee replacement system assembly fixtures comprises a femoral holder and a tibial holder. The cable-spring combination has predetermined mechanical properties of the ligament, tendon, or muscle component which it represents. Such mechanical properties include tensile stiffness, viscoelasticity, strain, strength and yield modulus.

The kinematic restraint device of the present invention overcomes hurdles posed by the use of natural knees in determining the range of motion of a total knee replacement system. It also simulates passive soft tissue restraints of the natural knee in response to exterior perturbations. A first preferred embodiment delineates a total knee replacement system in the presence of ligaments related to the human knee. A second preferred embodiment deals with a total knee replacement system in the presence of both ligaments and a patellar tendon. In a third preferred embodiment, a total knee replacement system is operated in the presence of ligaments and quadriceps muscle activity. A fourth preferred embodiment involves a total knee replacement system ensheathed by an outer membrane to simulate the combined damping effects of fibrous structures, fatty tissues, and muscle mass enveloping the knee joint on the total knee replacement kinematics. Because these kinematic restraint devices provide a base for a stable set of reproducible conditions that can be quantitatively measured, the function of a total knee replacement system can therefore be estimated for the same set of predetermined conditions.

Figure 1:
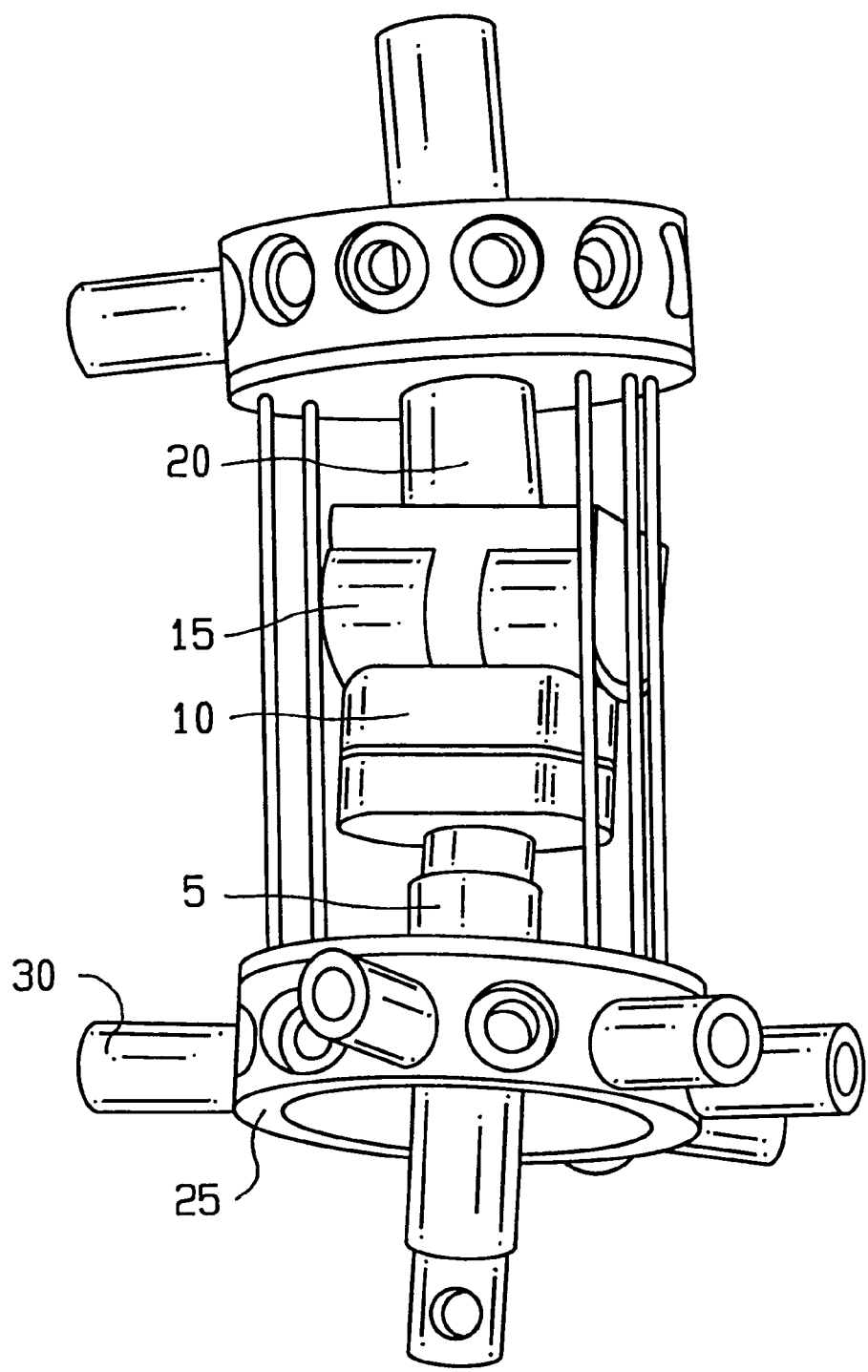
FIG. 1 is a schematic diagram of a kinematic restraint device of a first embodiment of the invention.

FIG. 1 is a schematic diagram of a first preferred embodiment of the kinematic restraint device. The total knee replacement system comprises a femoral component 15 and a tibial component 10, each of which has a contact surface. The contact surface of the femoral component is in contact with the contact surface of the tibial component to form a condyloid joint that simulates a human knee. The set of total knee system assembly fixtures comprises a femoral holder 20 and a tibial holder 5. The femoral component is affixed to one end of the femoral holder, and the tibial component is affixed to one end of the tibial holder.

At least one cable-spring combination is used in the operation of the kinematic restraint device to represent at least a ligament selected from the group consisting of the anterior cruciate ligament, the posterior cruciate ligament, the medial collateral ligament, and the lateral collateral ligament. A preferred embodiment of the spring used is a hollow compressive cylindrical core made of a polymeric material. The material chosen for the spring has predetermined compressive properties to simulate the tensile properties of a specific ligament of the human knee. As an alternative embodiment, the cable can be made of a material that has the predetermined mechanical properties of the ligament.

The cable-spring combination is mounted on the femoral holder and the tibial holder using cylindrical collars and cable assemblies. On the tibial portion, a cylindrical collar 25 is affixed to the tibial holder by set screws. The collar has a cylindrical surface and a circular flange attached at one of its bottoms. A plurality of through-holes are made on the circular flange of the collar (not shown). The diameter of the hole is made big enough to allow the cable to move freely through the hole. The cylindrical surface of the collar has a plurality of counterbored through-holes oriented perpendicular to the axis of the cylindrical collar. The diameter of the hole is made big enough to also allow the cable to move freely through the hole, while the diameter of the counterbore is made big enough to secure a compression spring 30 at its first end.

As evident from FIG. 1, a similar arrangement of the cylindrical collar is used on the femoral portion of the kinematic restraint device.

Figure 2:
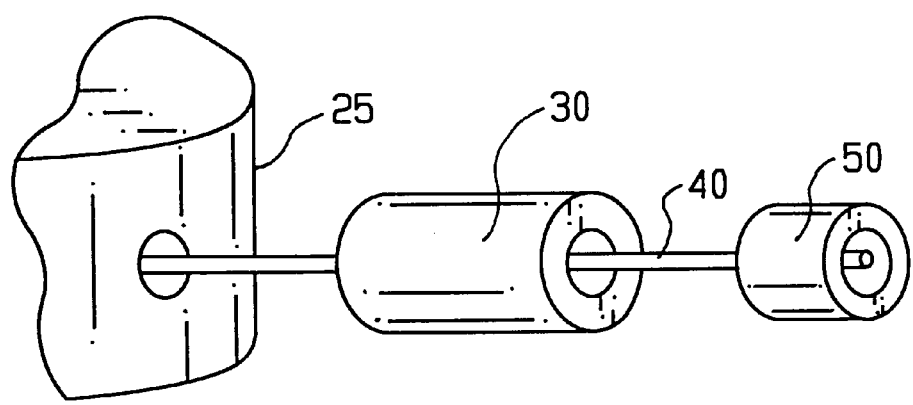
FIG. 2 is a schematic diagram of a cable assembly used in a kinematic restraint device of the invention.

A cable assembly includes an end fitting. As shown in FIG. 2, a cable 40 is attached to an end fitting 50. The end fitting is movably attached to the second end of the compression spring 30. Referring to FIG. 1, the cable goes through the cylindrical core of the compression spring and a hole in the cylindrical surface of the collar affixed to the tibial holder. The cable then extends through a hole in the flange of the collar. When the cable reaches the femoral portion, it sequentially passes through a hole in the flange of a cylindrical collar, a hole in a cylindrical surface of the collar, a compression spring, and finally it terminates at another end fitting. The end fittings are used to modify the cable length to replicate the resting length of a ligament of the human knee. The location of the holes on the flange represents various anatomical placements for specific ligaments of the human knee.

It is preferred that a plurality of cables are used simultaneously to represent a multistrand aspect of a single ligaments. It is also preferred that two, three, or four cable-spring combinations are used simultaneously to represent more than one ligament.

In an operation to determine the range of motion of a total knee replacement system, the total knee replacement system having a femoral and tibial components as described above is used. At least one cable-spring combination is affixed to a femoral and tibial holders to represent at least one ligament component. The cable-spring combination is calibrated to have predetermined mechanical properties of the ligament. The resting length of the cable-spring combination is also calibrated to have a predetermined length, characteristic of the ligament. As the total knee replacement system is subjected to an external force or torque profile, the resulting motion is dictated in part by the stiffness and the three-dimensional orientation of each cable assembly. Linear and rotational tibiofemoral displacements are recorded during the application of the force and torque profile, and plotted against each other. These data are then used to compare the range of motion of a total knee replacement system to the range of motion of a natural knee as measured under similar force and torque profiles. Moreover, these data are compared for the kinematic signatures of different total knee replacement systems.

Figure 3:
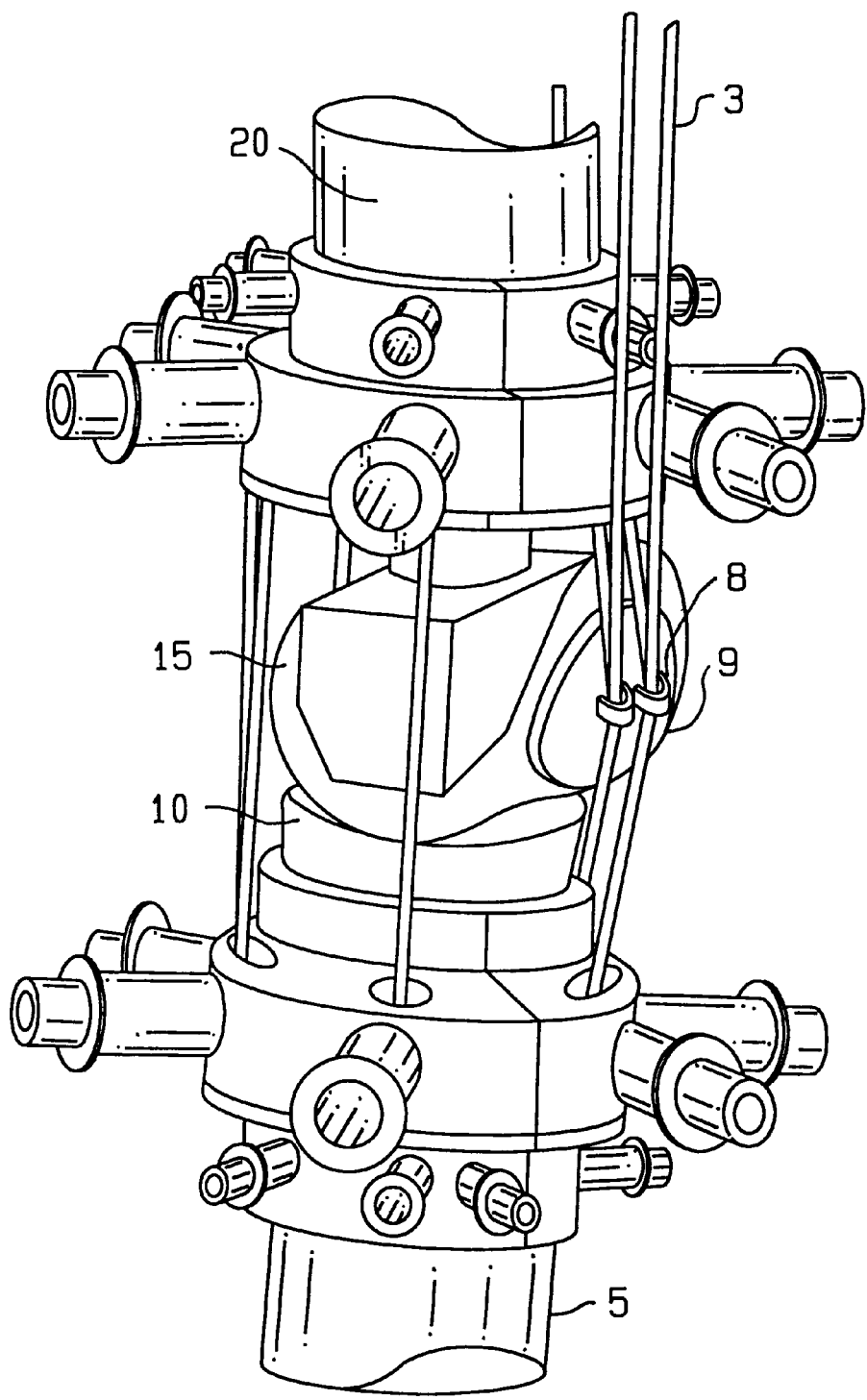
FIG. 3 is a schematic diagram of a kinematic restraint device of one of a second and third embodiments of the invention.

The second embodiment of the invention is used to assess the function of the total knee replacement system under the presence of both ligaments and the patellar tendon of the knee. Referring to FIG. 3, the total knee replacement system further comprises a patellar component 9 having a contact surface. The patellar component is positioned anteriorly and superiorly on the condyloid joint formed of the femoral 15 and tibial 10 components. The contact surface of the patellar component is in contact with the contact surface of the femoral component to form a patellofemoral joint to simulate a partial arthrodial articulation.

At least one cable-spring combination is used in the operation of kinematic restraint device to represent at least a ligament selected from the group consisting of the anterior cruciate ligament, the posterior cruciate ligament, the medial collateral ligament, and the lateral collateral ligament. The cable-spring combination is mounted on the femoral holder and the tibial holder in a similar way as disclosed in the first embodiment.

It is preferred to simultaneously use both the cable-spring combination for the ligament and a cable for the patellar component. In this preferred case, as shown in FIG. 3, a cable 3 connects the patellar component to the femoral holder 20 and the tibial holder 5 via a fastener 8. This cable has predetermined mechanical properties that allows normal patellar tracking similar to that of a natural knee.

The kinematic restraint device of this embodiment is operated in the same manner as that in the first embodiment to determine the functions of the tibiofemoral and patellofemoral articulations of the total knee replacement system.

The third embodiment of the invention is used to assess the function of the total knee replacement system under the presence of both ligaments and the quadriceps muscle. Referring to FIG. 3, the total knee replacement system further comprises a patellar component 9 having a contact surface. The patellar component is positioned anteriorly and superiorly on the condyloid joint formed of the femoral 15 and tibial 10 components. The contact surface of the patellar component is in contact with the contact surface of the femoral component to form a patellofemoral joint to simulate a partial arthrodial articulation.

At least one cable-spring combination is used in the operation of the kinematic restraint device to represent at least one ligament selected from the group consisting of the anterior cruciate ligament, the posterior cruciate ligament, the medial collateral ligament, and the lateral collateral ligament. Furthermore, at least one cable 3 connects the patellar component to the tibial holder 5 and to an actuator (not shown) via a fastener 8 to simulate the action of the quadriceps muscle.

Figure 4:
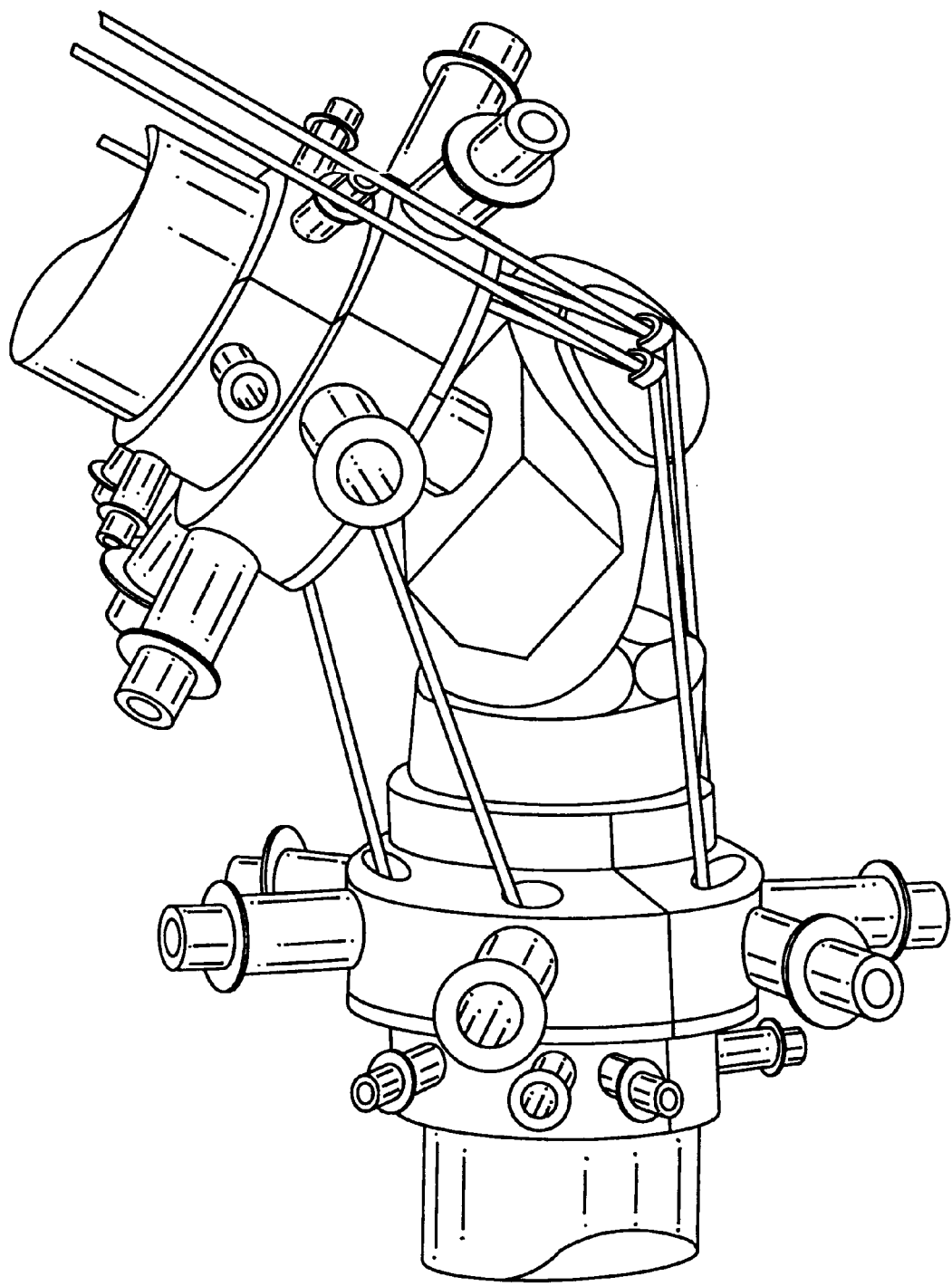
FIG. 4 is a schematic diagram of a kinematic restraint device of a second or third embodiment of the invention when an external force is applied thereto.

FIG. 4 depicts a kinematic restraint device of the third embodiment of the invention when an external force or torque profile is applied thereto. In operation, the cable-spring combination and the cable representing both the ligament and the quadriceps muscle are initially set up to have predetermined mechanical properties of the ligament and quadriceps muscle which it represents. Such mechanical properties include tensile stiffness, viscoelasticity, strain, strength and yield modulus. The actuator applies tensile forces similar to those applied by the quadriceps muscle group in a natural knee. As the total knee replacement system is subjected to definite force or torque profiles, the resulting motion is dictated in part by the stiffness and three-dimensional orientation of each cable assembly. The linear and rotational tibiofemoral displacements are recorded during the application of the forces and torques and plotted against each other. These data are then used to compare the range of motion of a total knee replacement system to the range of motion of a natural knee as measured under similar force and torque profiles. These data are further used to compare the kinematic signatures of different prosthetic component designs.

It is preferred that a plurality of cable-spring combinations are used simultaneously to represent a multistrand aspect of a single ligament. It is also preferred that two, three or four cable-spring combinations are used simultaneously to represent more than one ligament.

Figure 5:
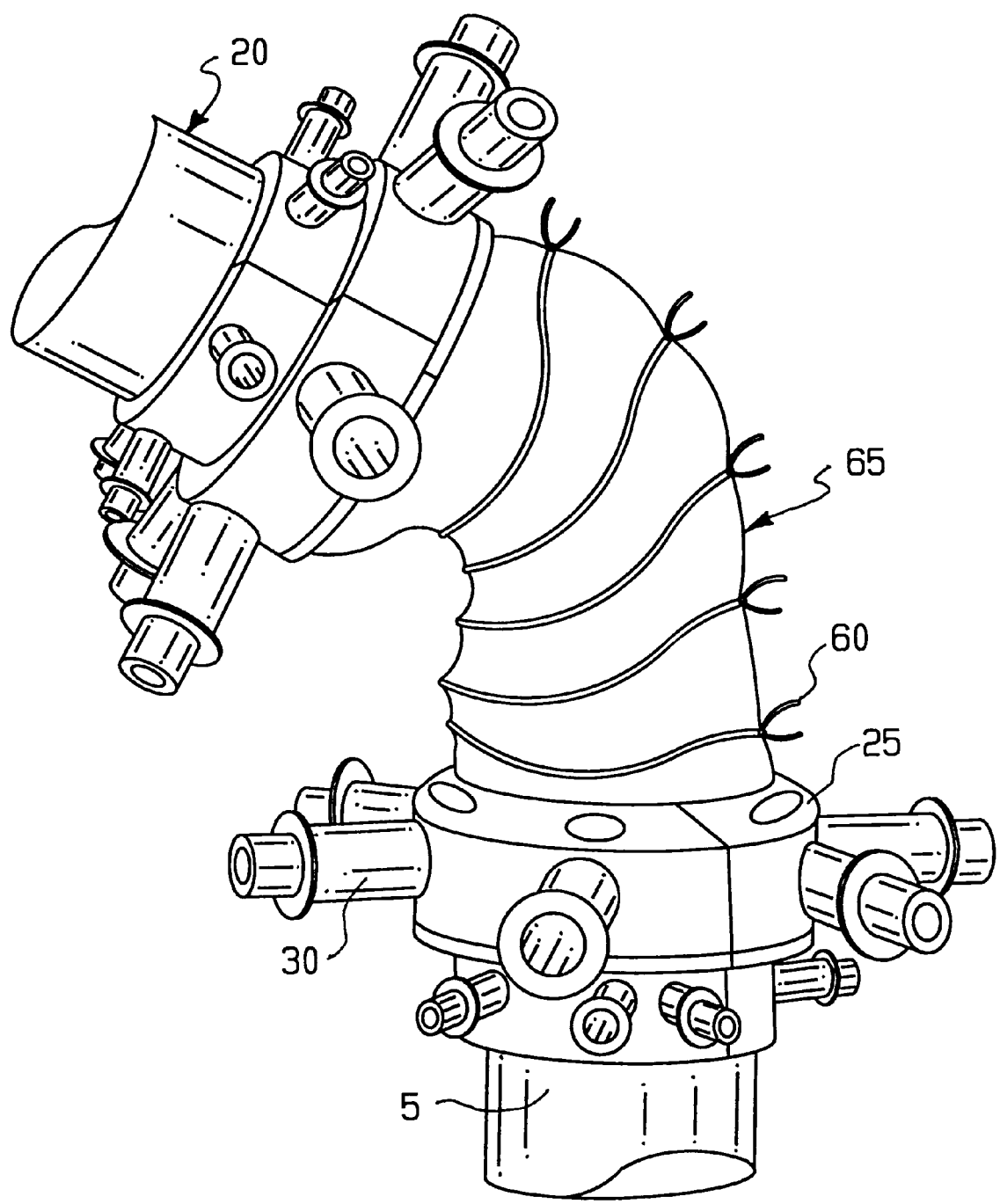
FIG. 5 is a schematic diagram of a kinematic restraint device of a fourth embodiment of the invention.

In a fourth preferred embodiment, the kinematic restraint device for determining the range of motion of a total knee replacement system according to the present invention further comprises an outer membrane. The outer membrane ensheathes the total knee replacement system and the cable to simulate the damping effects of other fibrous structures, fatty tissues, and muscle mass enveloping the knee joint on the total knee replacement kinematics. FIG. 5 depicts the kinematics restraint device with an outer membrane thereon.

Figure 6:
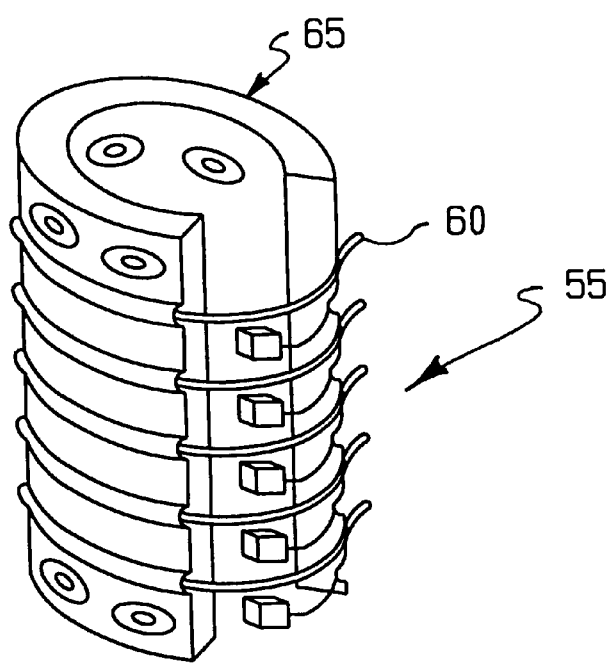
FIG. 6 is a schematic diagram of an outer membrane used in the kinematic restraint device of the fourth embodiment of the invention.

Referring to FIG. 6, the outer membrane 55 comprises a composite structure 65 and a plurality of flexible tensioners 60 embedded therein. The composite structure helps guide the cables by means of the flexible tensioners. A material with anisotropic properties such as neoprene can be used for the composite structure. The composite structure can be filled with gel or other material to further approximate non-linear properties exhibited by soft tissues.

It is understood that various other modifications will be readily apparent to those skilled in the art without departing from the scope and spirit of the invention. Accordingly, it is not intended that the scope of the claims appended hereto be limited to the description set forth herein, but rather that the claims be construed as encompassing all the features of the patentable novelty that reside in the present invention, including all features that would be treated as equivalents thereof by those skilled in the art to which this invention pertains.

What is claimed is:

1. A kinematic restraint device for determining the range of motion of a total knee replacement system, comprising:
   a. a set of total knee replacement system assembly fixtures including
      i. a femoral holder, and
      ii. a tibial holder;
   b. a total knee replacement system including
      i. a femoral component, affixed to one end of said femoral holder, having a contact surface, and
      ii. a tibial component, affixed to one end of said tibial holder, having a contact surface, said contact surface of said femoral component being in contact with said contact surface of said tibial component to form a condyloid joint to simulate a human knee;
   c. at least one combination of a cable and a spring connected thereto representing at least one ligament component related to the human knee, said cable-spring combination having predetermined mechanical properties of said ligament component;
   d. means for affixing said cable-spring combination on said femoral holder; and
   e. means for affixing said cable-spring combination on said tibial holder.

2. The kinematic restraint device according to claim 1, wherein said cable-spring combination represents a ligament selected from the group consisting of the anterior cruciate ligament, the posterior cruciate ligament, the medial collateral ligament, and the lateral collateral ligament.

3. The kinematic restraint device according to claim 2, wherein a plurality of said cable-spring combinations are used simultaneously to represent respectively more than one member of said group of ligament components.

4. The kinematic restraint device according to claim 2, wherein a plurality of said cable-spring combinations are used simultaneously to represent a multistrand aspect of one member of said group of ligament components.

5. The kinematic restraint device according to claim 1, wherein said predetermined mechanical properties include tensile stiffness, viscoelasticity, strain, strength and yield modulus.

6. The kinematic restraint device according to claim 1, further comprising an outer membrane ensheathing said total knee replacement system and said cable.

7. The kinematics restraint device according to claim 6, wherein said outer membrane comprises a composite structure and a plurality of flexible tensioners embedded therein.

8. The kinematic restraint device according to claim 1, wherein said means for affixing said cable-spring combination on said femoral holder comprises:
   a. a cylindrical collar affixed to said femoral holder by a plurality of set screws, a first end of said spring being positioned around said cylindrical collar; and
   b. a cable assembly, positioned at a second end of said spring, comprising an end fitting for manipulating said cable.

9. The kinematic restraint device according to claim 1, wherein said means for affixing said cable-spring combination on said tibial holder comprises:
   a. a cylindrical collar affixed to said tibial holder by a plurality of set screws, a first end of said spring being positioned around said cylindrical collar; and
   b. a cable assembly, positioned at a second end of said spring, comprising an end fitting for manipulating said cable.

10. A kinematic restraint device for determining the range of motion of a total knee replacement system, comprising:
   a. a set of total knee system assembly fixtures including
      i. a femoral holder, and
      ii. a tibial holder;
   b. a total knee replacement system including
      i. a femoral component, affixed to one end of said femoral holder, having a contact surface,
      ii. a tibial component, affixed to one end of said tibial holder, having a contact surface, said contact surface of said femoral component being in contact with said contact surface of said tibial component to form a condyloid joint to simulate a human knee, and
      iii. a patellar component, positioned anteriorly and superiorly on said condyloid joint, having a contact surface, said contact surface of said patellar component being in contact with said contact surface of said femoral component to form a patellofemoral joint to simulate a partial arthrodial articulation;
   c. at least one combination of a cable and a spring connected thereto representing at least one ligament, tendon, or muscle component related to the human knee, said cable-spring combination having predetermined mechanical properties of said ligament, tendon or muscle component;
   d. means for affixing said cable-spring combination on said femoral holder; and
   e. means for affixing said cable-spring combination on said tibial holder.

11. The kinematic restraint device according to claim 10, wherein said cable-spring combination represents one of the group consisting of the anterior cruciate ligament, the posterior cruciate ligament, the medial collateral ligament, the lateral collateral ligament, the patellar tendon and the quadriceps muscle.

12. The kinematic restraint device according to claim 11, wherein a plurality of said cable-spring combinations are used simultaneously to represent more than one member of said group of ligament, tendon, and muscle components.

13. The kinematic restraint device according to claim 11, wherein a plurality of said cable-spring combinations are used simultaneously to represent a multistrand aspect of one member of said group of ligament, tendon, and muscle components.

14. The kinematic restraint device according to claim 10, wherein said predetermined mechanical properties include tensile stiffness, viscoelasticity, strain, strength and yield modulus.

15. The kinematic restraint device according to claim 10, further comprising an outer membrane ensheathing said total knee replacement system and said cable.

16. A method for determining the range of motion of a total knee replacement system, comprising:
   a. providing a set of total knee replacement system assembly fixtures including
      i. a femoral holder, and
      ii. a tibial holder;
   b. providing a total knee replacement system including
      i. a femoral component, affixed to one end of said femoral holder, having a contact surface, and
      ii. a tibial component, affixed to one end of said tibial holder, having a contact surface, said contact surface of said femoral component being in contact with said contact surface of said tibial component to form a condyloid joint to simulate a human knee;
   c. using at least one combination of a cable and a spring connected thereto to represent at least one ligament component related to the human knee selected from the group consisting of the anterior cruciate ligament, the posterior cruciate ligament, the medial collateral ligament, and the lateral collateral ligament;
   d. affixing said cable-spring combination on said femoral holder;
   e. affixing said cable-spring combination on said tibial holder;
   f. calibrating said cable-spring combination to have predetermined mechanical properties of said ligament component;
   g. calibrating the resting length of said cable-spring combination to have a predetermined length, characteristic of said ligament component;
   h. measuring the linear and rotational tibiofemoral displacements when said total knee replacement system is subjected to externally applied force or torque profiles; and
   i. determining from said tibiofemoral displacements the range of motion of said total knee replacement system.

17. The method for determining the range of motion of a total knee replacement system according to claim 16, wherein a plurality of said cable-spring combinations are used simultaneously to represent more than one member of said group of ligament components.

18. The method for determining the range of motion of a total knee replacement system according to claim 16, wherein a plurality of said cable-spring combinations are used simultaneously to represent a multistrand aspect of one member of said group of ligament components.

19. A method for determining the range of motion of a total knee replacement system, comprising:
   a. providing a set of total knee system assembly fixtures including
      i. a femoral holder, and ii. a tibial holder;
b. providing a total knee replacement system including
   i. a femoral component, affixed to one end of said femoral holder, having a contact surface,
   ii. a tibial component, affixed to one end of said tibial holder, having a contact surface, said contact surface of said femoral component being in contact with said contact surface of said tibial component to form a condyloid joint to simulate a human knee, and
   iii. a patellar component, positioned anteriorly and superiorly on said condyloid joint, having a contact surface, said contact surface of said patellar component being in contact with said contact surface of said femoral component to form a patellofemoral joint to simulate a partial arthrodial articulation;
c. using at least one combination of a cable and a spring connected thereto to represent at least one ligament, tendon, or muscle component related to the human knee selected from the group consisting of the anterior cruciate ligament, the posterior cruciate ligament, the medial collateral ligament, the lateral collateral ligament, the patellar tendon and the quadriceps muscle;
d. affixing said cable-spring combination on said femoral holder;
e. affixing said cable-spring combination on said tibial holder;
f. calibrating said cable-spring combination to have predetermined mechanical properties of said ligament, tendon, or muscle component;
g. calibrating the resting length of said cable-spring combination to have a predetermined length characteristic of said ligament, tendon or muscle component;
h. measuring the linear and rotational tibiofemoral and patellofemoral displacements when said total knee replacement system is subjected to externally applied force or torque profiles; and
i. determining from said tibiofemoral and patellofemoral displacements the range of motion of said total knee replacement system.

20. The method of determining the range of motion of a total knee replacement system according to claim 19, wherein a plurality of said cable-spring combinations are used simultaneously to represent more than one member of said group of ligament, tendon, or muscle component.

21. The method of determining the range of motion of a total knee replacement system according to claim 19, wherein a plurality of said cable-spring combinations are used simultaneously to represent a multistrand aspect of one member of said group of ligament, tendon, or muscle component.

22. A method for determining the range of motion of a total knee replacement system, comprising:

a. providing a set of total knee system assembly fixtures including
   i. a femoral holder, and
   ii. a tibial holder
b. providing a total knee replacement system including
   i. a femoral component, affixed to one end of the said femoral holder, having a contact surface,
   ii. a tibial component, affixed to one end of said tibial holder, having a contact surface, said contact surface of said femoral component being in contact with said contact surface of said tibial component to form a condyloid joint to simulate a human knee, and
   iii. a patellar component, positioned anteriorly and superiorly on said condyloid joint, having a contact surface, said contact surface of said patellar component being in contact with said contact surface of said femoral component to form a patellofemoral joint to simulate a partial arthrodial articulation;
c. using at least one combination of a cable and a spring connected thereto to represent at least one ligament component related to the human knee selected from the group consisting of the anterior cruciate ligament, the posterior cruciate ligament, the medial collateral ligament, and the lateral collateral ligament;
d. affixing said cable-spring combination on said femoral holder;
e. affixing said cable-spring combination on said tibial holder;
f. using at least one cable representing the patellar tendon of the human knee, wherein said cable has predetermined mechanical properties of the patellar tendon;
g. using an actuator to apply tensile forces similar to those applied by the quadriceps muscle group in the natural knee;
h. affixing said cable on said tibial holder;
i. affixing said cable on said actuator;
j. calibrating said cable-spring combination to have predetermined mechanical properties of said ligament;
k. calibrating the resting length of said cable-spring combination to have a predetermined length, characteristic of said ligament;
l. measuring the linear and rotational tibiofemoral and patellofemoral displacements when said total knee replacement system is subjected to externally applied force or torque profiles; and
m. determining from said tibiofemoral and patellofemoral displacements the range of motion of said total knee replacement system.

* * * * *